United States Patent [19]

Samejima et al.

[11] Patent Number: 4,542,042

[45] Date of Patent: Sep. 17, 1985

[54] PROCESS FOR PREPARING FREE-FLOWING ETHYLCELLULOSE MICROCAPSULES

[75] Inventors: Masayoshi Samejima, Minoh; Goichi Hirata, Yawata; Takashi Ishibashi, Sakai, all of Japan

[73] Assignee: Tanabe Seiyaku Co., Ltd., Osaka, Japan

[21] Appl. No.: 510,202

[22] Filed: Jul. 1, 1983

[30] Foreign Application Priority Data

Jul. 16, 1982 [JP] Japan .................... 57-124829

[51] Int. Cl.$^4$ .............................................. B05D 7/00
[52] U.S. Cl. .................... 427/213.36; 252/315.3; 264/4.1; 427/213.3; 428/402.2; 428/402.21; 428/402.24
[58] Field of Search .............. 264/4.1; 427/213.3, 427/213.36; 428/402.2, 402.21, 402.24; 252/315.3

[56] References Cited

U.S. PATENT DOCUMENTS

| | | | |
|---|---|---|---|
| 3,341,416 | 9/1967 | Anderson et al. | 167/83 |
| 3,626,056 | 12/1971 | Granatek et al. | 424/35 |
| 3,943,063 | 3/1976 | Morishita et al. | 264/4.1 |
| 4,123,382 | 10/1978 | Morse et al. | 427/213.32 |
| 4,218,333 | 8/1980 | Samejima et al. | 252/316 |
| 4,389,331 | 6/1983 | Samejima et al. | 427/213.3 |

FOREIGN PATENT DOCUMENTS

| | | |
|---|---|---|
| 152739 | 11/1981 | Japan . |
| 898668 | 6/1962 | United Kingdom . |
| 920866 | 3/1963 | United Kingdom . |

OTHER PUBLICATIONS

Small, "Some Factors Affecting the Solubility of Polymers", J. Appl. Chem., Feb. 3, 1953, pp. 71–80.
D'Onofrio et al., "Encapsulated Microcapsules", International Journal of Pharmaceutics, 2 (1979), 91–99.

*Primary Examiner*—Paul Lieberman
*Assistant Examiner*—Robert A. Wax
*Attorney, Agent, or Firm*—Jordan B. Bierman

[57] ABSTRACT

A process for preparing free-flowing microcapsules by taking advantage of the phase-separation of ethylcellulose in cyclohexane is disclosed. In this process, a hydrocarbon compound which is soluble in cyclohexane and have a molecular weight of 150 to 3,000 and a solubility parameter ($\delta$, at 25° C.) of 7 to 10 (cal/cm$^3$)$^{\frac{1}{2}}$ is used as the phase-separation-inducing agent.

19 Claims, No Drawings

PROCESS FOR PREPARING FREE-FLOWING ETHYLCELLULOSE MICROCAPSULES

This invention relates to a process for preparing free-flowing ethylcellulose microcapsules.

It is known that in preparing microcapsules by taking advantage of the phase-separation of ethylcellulose in cyclohexane, butyl rubber having a Mooney viscosity (ML-8/100° C.) of 60 to 75, polybutadiene having a molecular weight of 8,000 to 10,000, polyethylene having a molecular weight of 7,000 or polyisobutylene having a molecular weight of 8,700 to 135,000 are used as the phase-separation-inducing agent [Japanese Patent Publication (examined) Nos. 528/1967 and 30136/1970, U.S. Pat. No. 3,341,416].

However, for industrial production of microcapsules these known methods are still unsatisfactory in that it is difficult to recover free-flowing discrete microcapusules in a high yield because microcapsules formed in the microencapsulation step is liable to agglomerate together into a large lump each containing a myriad of individual capsules and also stick to apparatuses for production of microcapsules. Additionally, when butyl rubber, polybutadiene or polyisobutylene having a molecular weight of not less than 7,000 is used as the phase-separation-inducing agent, the removal of said agent from the microcapsules obtained can be effected only by washing the microcapsules with the large excess (e.g., 50 ml/g) of cyclohexane for a long time because of their high adhesiveness and slow velocity of dissolution in the solvent. Further, in making such microcapsules, as long as 4 to 10 hours are required to dissolve only one gram of the above-mentioned agent (i.e., butyl rubber, polybutadiene or polyisobutylene having a molecular weight of not less than 7,000) in 30 ml of cyclohexane at 80° C. This inevitably impairs the operational efficiency in making the microcapsules. On the other hand, when polyethylene having a molecular weight of not less than 7,000 is used as the phase-separation-inducing agent, said polyethylene is separated as minute particles during cooling the dispersion and deposited on and in the wall of the microcapsules. Since such minute particles of polyethylene can not be washed out completely with a poor solvent such as cyclohexane and can not be separated from the microcapsules by passing through a sieve, therefore, such polyethylene is not suitable for use as the phase-separation-inducing agent in making microcapsules having a particle size less than 100 μm.

As an alternative to the above-mentioned methods, U.S. Pat. No. 4,218,333 discloses a method of making microcapsules by using a mixture of polyisobutylene having a molecular weight of 8,000 to 12,000 and polyisobutylene having a molecular weight of 60,000 to 140,000 as the phase-separation-inducing agent. In this method, however, it is still difficult to completely remove the polyisobutylene from the formed microcapsules by washing them with a solvent such as cyclohexane or n-hexane because of its poor solubility in the solvent. It is also difficult to control the thickness of the ethylcellulose walls and obtain microcapsules having complete and compact walls.

As a result of various investigations for seeking a method free from the foregoing disavantages of the known methods, we have now found that free-flowing ethylcellulose microcapsules having compact and complete walls can be readily obtained by carrying out the liquid-liquid phase separation of ethylcellulose in cyclohexane in the presenece of a hydrocarbon compound which is soluble in cyclohexane and has a molecular weight of 150 to 3,000 and a solubility parameter ($\delta$, at 25° C.) of 7 to 10 $(cal/cm^3)^{\frac{1}{2}}$. Namely, when said hydrocarbon compound is used as the phase-separation-inducing agent instead of those known in the art, no substantial adhesion or agglomeration of each microcapsules takes place in the microencapsulation step.

According to the present invention, free-flowing microcapsules can be prepared by the steps of:

(i) dispersing particles of a core material in a cyclohexane solution containing ethylcellulose and a hydrocarbon compound, said hydrocarbon compound being soluble in cyclohexane and having a molecular weight of 150 to 3,000 and a solubility parameter ($\delta$, at 25° C.) of 7 to 10 $(cal/cm^3)^{\frac{1}{2}}$, (ii) cooling the dispersion until the ethylcellulose separates out from the dispersion to form coating walls on and around the particles of said core material, and then (iii) recovering the thus-formed microcapsules therefrom.

A wide variety of hydrocarbon compounds which are soluble in cyclohexane and have a molecular weight of 150 to 3,000, especially 150 to 1,000, more specially 160 to 600 and a solubility parameter of 7 to 10 $(cal/cm^3)^{\frac{1}{2}}$, especially 7.5 to 9.5 $(cal/cm^3)^{\frac{1}{2}}$, more especially 8.0 to 9.2 $(cal/cm^3)^{\frac{1}{2}}$, can be used as the phase-separation-inducing agent in the present invention. As shown in J. Appl. Chem., Vol.3, pp 71–80 (1953), the solubility parameter ($\delta$, at 25° C.) is given by the following formula:

$$\delta = \frac{\Sigma F}{V} = \left(\frac{E}{V}\right)^{\frac{1}{2}}$$

wherein F is Small's molar-attraction constant at 25° C., V is molar volume and E is molar cohesive energy.

Examples of the hydrocarbon compounds to be used as the phase-separation-inducing agent in the present invention include, for example, liquid paraffin, petroleum jelly, ceresin, paraffin, microcrystalline wax, squalane, squalene, pristane, polybutadiene (Molecular weight: 500 to 3,000), polybutene (Molecular weight: 200 to 3,000), polyisoprene (Molecular weight: 1,000 to 3,000) and butadiene-styrene copolymer (Molecular weight: 1,500 to 3,000). Among these hydrocarbon compounds, a preferred subgenus is liquid paraffin, paraffin and polybutene (Molecular weight: 200 to 2,500). The most preferred subgenus is liquid paraffin. It is preferred to use 0.1 to 20 g, especially 1 to 10 g, more especially 1 to 3 g, of the hydrocarbon compound per 100 ml of cyclohexane.

On the other hand, ethylcellulose having an ethoxy content of 46.5 to 55 w/w % is preferably used as the wall-forming material of the present invention. It is also preferred that the viscosity of said ethylcellulose when measured at 25° C. with respect to a 5 w/w % solution of it in toluene-ethanol (4:1) is within the range of 3 to 500 cP, especially 40 to 120 cP. It is also preferred that said ethylcellulose is used in an amount of 0.03 to 5 grams, especially 0.05 to 0.5 gram, per gram of the core material used.

Any one of pharmaceutically active compounds (or medicaments) can be used as the core material to be microencapsulated in the present invention. Such pharmaceutically active compound or medicament to be microencapsulated may be either solid, gel or semi-solid. In order to prepare a homogeneous dispersion at the microencapsulation step, it is preferred that said pharmaceutically active compound or medicament has a particle size of about 5 to about 1000 μm, especially 50 to 500 μm. Eligible for microencapsulation as solids are particles of material such as, for example, vitamins (e.g., ascorbic acid), amino acids (e.g., potassium aspartate, magnesium aspartate), minerals (e.g., potassium chloride), anti-microbial agents (e.g., benzylpenicillin potassium salt, sulfomethiazole), anti-tumor agents (e.g., 5-fluorouracil, bleomycin hydrochloride), metabolic agents (e.g., glutathione), cardiovascular agents (e.g., diltiazem hydrochloride), analgesics (e.g., acetylsalicylic acid), anti-histaminics (e.g., diphenhydramine hydrochloride), neuro-psychotropic agents (e.g., calcium N-(γ,γ-dihydroxy-β,β-dimethylbutyryl)-γ-aminobutyrate), agents affecting digestive organs (e.g., methylmethionine sulfonium chloride, timepidium bromide, precipitated calcium carbonate, 2-dimethylamino-2-phenylbutyl 3,4,5-trimethoxybenzoate hydrogen maleate), agents affecting respiratory organs (e.g., trimethoquinol hydrochloride, 1-methyl-5-methoxy-3-(dithien-2-ylmethylene)piperidine hydrobromide) and so forth. Also eligible for microencapsulation as semi-solids are, for example, slurrys such as a slurry composed of 30 w/w % of sodium polyacrylate, 40 w/w % of water and 30 w/w % of 5-fluorouracil. And pharmaceutically active compounds in the form of "gel" which can be microencapsulated include, for example, dextran gel having a medicament (e.g., methylmethionine sufonium chloride) adsorbed therein, formalin-treated gelatin gel having dispersed a medicament (e.g., sulfamethomidine) therein, and so forth.

In making the microcapsules in accordance with the present invention, particles of a core material are first dispersed in cyclohexane containing ethylcellulose and the hydrocarbon compound. This dispersing step is preferably carried out by adding ethylcellulose, the hydrocarbon compound and particles of a core material to cyclohexane under stirring and then heating the mixture to 75° to 80° C. Said dispersing step is also carried out by dissolving ethylcellulose and the hydrocarbon compound in cyclohexane at 75° to 80° C. and then dispersing particles of a core material in the solution under stirring. It is preferred to use the ethylcellulose so that the concentration of said ethylcellulose in cyclohexane becomes 0.5 to 10 w/v %, especially 1 to 5 w/v %. When the thus-prepared dispersion is then cooled gradually (e.g., at a rate of 0.05° to 4° C., especially 0.5° to 2° C., per minute) under continuous stirring at 100 to 400 rpm, ethylcellulose in the form of "gel" separates out from the dispersion at about 70° to 55° C. mainly by coacervation thereof thereby depositing on or wrapping the particles of the core material, and the ethylcellulose gel thus deposited forms seamless walls. When the temperature is further lowered to a temperature not higher than 40° C. (e.g., 40° to 20° C.), the thus-formed embryonic microcapsules are shrunken and become solid by solvent loss from the capsule walls, thus giving stable microcapsules. Once stable microcapsules are formed, a poor solvent such as cyclohexane, petroleum-ether or n-hexane may be, if necessary, added to the dispersion to further stabilize the microcapsules.

In the above-mentioned method of the present invention, the hydrocarbon compound to be used as the phase-separation-inducing agent may be used in combination with a hydrocarbon polymer (e.g., polyethylene, butyl rubber, polybutadiene, polyisobutylene) having a molecular weight of 4,000 to 2,000,000 and/or an organopolysiloxane (e.g., dimethyl polysiloxane, diphenyl polysiloxane, polystyrene-polydimethylsiloxane block copolymer). The organopolysiloxane to be used in the present invention may be a mixture of 99 to 50 w/w % of the above-mentioned organopolysiloxane and 1 to 50 w/w % of additives such as silicon dioxide, titanium oxide, calcium stearate or talc. It is preferred to add said hydrocarbon polymer and/or organopolysiloxane to cyclohexane at the stage of addition of ethylcellulose and the hydrocarbon compound. Suitable amount of the hydrocarbon polymer to be added is 0.1 to 10 grams, especially 1 to 3 grams, per 100 ml of cyclohexane. On the other hand, the organopolysiloxane is preferably used in an amount of 0.01 to 10 grams, especially 0.1 to 3 grams, per 100 ml of cyclohexane.

The microcapsules thus obtained may be recovered by conventional manners such as, for example, decantation, filtration, centrifugation and so forth. In addition, free-flowing discrete microcapsules which are substantially free from the hydrocarbon compound, the hydrocarbon polymer and the organopolysiloxane can be readily obtained by washing the thus-obtained microcapsules with cyclohexane, petroleum-ether, n-hexane and so forth, i.e., with an organic solvent which dissolves the hydrocarbon compound, the hydrocarbon polymer and the organopolysiloxane but does not dissolve both of ethylcellulose and the core material used.

According to the above-mentioned method of the present invention, the hydrocarbon compound which is used as the phase-separation-inducing agent binds to molecules of ethylcellulose through the interaction thereof such as van der Waals force to deposit on and around the core material. The deposited hydrocarbon compound induces coacervation of ethylcellulose without causing flocculation of ethylcellulose and at the same time prevents the formed microcapsules from adhering and agglomerating together. Further, according to the present invention, free-flowing discrete microcapsules having complete and compact walls can be obtained in such a high yield as over 90% and the operational efficiency in making microcapsules is remarkably improved because the formed microcapsules neither agglomerate together nor stick to apparatuses for production thereof. After the microencapsulation step of the present invention, the hydrocarbon compound used can be readily removed from microcapsules by washing them with a solvent such as n-hexane because of high solubility of said compound in the solvent.

EXPERIMENT

Microcapsules containing timepidium bromide (Chemical name: 1,1-dimethyl-5-methoxy-3-(dithien-2-ylmethylene)piperidinium bromide) were prepared in accordance with the following method. The thus-obtained microcapsules (i.e., microcapsules which met the requirements of "Fine Granules" specified in THE PHARMACOPOEIA OF JAPAN 10th-Edition) were examined with respect to the yield of said microcapsules and the content of active ingredient (i.e., timepidium bromide) contained in said microcapsules.

(Method)

(1) Core material:

7 parts by weight of an aqueous 45 v/v % ethanol solution were added to a powder mixture of 10 parts by weight of timepidium bromide, 84 parts by weight of lactose and 6 parts by weight of white dextrin, and the mixture was kneaded and granulated in conventional manners. The granules were dried. The granules having a particle size of 105 to 350 μm were used as the core material.

(2) Preparation of microcapsules:

24 g of a phase-separation-inducing agent shown in the following Table 1, 20 g of ethylcellulose [ethoxy content: 48 w/w %, visocosity (measured at 25° C. with respect to a toluene-ethanol (4:1) solution containing 5 w/w % of said ethylcellulose): 100 cP] and 140 g of the core material prepared in paragraph (1) were added to 800 ml of cyclohexane. The mixture was stirred at 80° C. to give a dispersion of the core material. The dispersion was cooled to room temperature under sitrring at 300 rpm. The microcapsules thus formed were recovered by filtration, washed with n-hexane and dried. Said microcapsules were passed through the nest of JIS (Japanese Industrial Standard) standard sieve (500 μm aperture) and then the nest of JIS standard sieve (105 μm aperture). The microcapsules which passed through the former sieve but did not pass through the latter sieve were collected, whereby timepidium bromide-containing microcapsules which met the requirements of "Fine Granules" specified in THE PHARMACOPOEIA OF JAPAN 10th-Edition were obtained.

(Results)

The results are shown in the following Table 1.

TABLE 1

| Nos. | Phase-separation-inducing agents | Solubility parameter $\delta$ (cal/cm$^3$)$^{\frac{1}{2}}$ | Yield of microcapsules (g) | Amount of active ingredient contained in microcapsules (%) |
| --- | --- | --- | --- | --- |
| 1. | liquid paraffin | 8.3–9.1 | 157 | 8.76 |
| 2. | petroleum jelly | 8.0–8.7 | 155 | 8.75 |
| 3. | ceresin | 8.8–8.9 | 151 | 8.77 |
| 4. | paraffin | 9.0–9.3 | 149 | 8.77 |
| 5. | microcrystalline wax | 8.7–8.0 | 151 | 8.75 |
| 6. | squalane | 8.9 | 157 | 8.75 |
| 7. | squalene | 9.2 | 153 | 8.79 |
| 8. | pristane | 7.6 | 153 | 8.77 |
| 9. | polybutadiene (M.W. = 700) | 8.1 | 155 | 8.81 |
| 10. | polybutadiene (M.W. = 2,000) | 8.1 | 151 | 8.95 |
| 11. | polybutene (M.W. = 270) | 8.8 | 157 | 8.74 |
| 12. | polybutene (M.W. = 900) | 8.4 | 151 | 8.97 |
| 13. | polybutene (M.W. = 2,350) | 8.4 | 149 | 8.76 |
| 14. | cis-1,4-polyisoprene (M.W. = 2,000) | 8.1 | 147 | 8.78 |
| (Positive Control) | | | | |
| | polyisobutylene (M.W. = 10,000) | 7.9 | 45 | 8.75 |

Note: M.W. stands for molecular weight.

EXAMPLE 1

16.8 g of liquid paraffin ($\delta = 8.3$–9.1 (cal/cm$^3$)$^{\frac{1}{2}}$), 7.2 g of polyisobutylene (molecular weight: 4,000), 20 g of ethylcellulose [ethoxy content: 48 w/w %, viscosity (measured at 25° C. with respect to a toluene-ethanol (4:1) solution containing 5 w/w % of said ethylcellulose): 100 cP] and 140 g of trimebutine maleate (Chemical name: 2-dimethylamino-2-phenylbutyl 3,4,5-trimethoxybenzoate hydrogen maleate) having a particle size of 105–177 μm were added to 800 ml of cyclohexane. The mixture was stirred at 80° C. to give a dispersion of the core material (i.e., trimebutine maleate). The dispersion was cooled to room temperature (about 25° C.) under stirring at 400 rpm. The microcapsules thus formed were recovered by filtration, washed with n-hexane and dried. Then, said microcapsules were passed through the nest of JIS standard sieve (350 μm aperture), whereby 156 g of trimebutine maleate-containing microcapsules which met the requirements of "Pulvers" specified in THE PHARMACOPOEIA OF JAPAN 10th-Edition were obtained.

For comparision, microcapsules were prepared in the same manner as described above except that 24 g of polyisobutylene (molecular weight: 4,000) were used instead of 16.8 g of liquid paraffin and 7.2 g of polyisobutylene, whereby only 39 g of trimebutine maleate-containing microcapsules which met the requirements of "Pulvers" specified above were obtained.

EXAMPLE 2

Microcapsules were prepared in the same manner as described in Example 1 except that 12 g of liquid paraffin ($\delta = 8.3$–9.1 (cal/cm$^3$)$^{\frac{1}{2}}$) and 12 g of polyisobutylene (molecular weight: 10,000) were used instead of 16.8 g of liquid paraffin and 7.2 g of polyisobutylene (molecular weight: 4,000). 154 g of trimebutine maleate-containing microcapsules which met the requirements of "Pulvers" specified above were obtained.

EXAMPLE 3

Microcapsules were prepared in the same manner as described in Example 1 except that 24 g of polybutene (molecular weight: 1,000, $\delta = 8.4$ (cal/cm$^3$)$^{\frac{1}{2}}$) were used instead of 16.8 g of liquid paraffin and 7.2 g of polyisobutylene. 156 g of trimebutine maleate-containing microcapsules which met the requirements of "Pulvers" specified above were obtained.

EXAMPLE 4

Microcapsules were prepared in the same manner as described in Example 1 except that 7.2 g of dimethyl polysiloxane (Viscosity measured at 25° C.: 10,000 cSt) were used instead of polyisobutylene. 156 g of trimebutine maleate-containing microcapsules which met the requirements of "Pulvers" specified above were obtained.

EXAMPLE 5

16.8 g of liquid paraffin ($\delta = 8.3$–9.1 (cal/cm$^3$)$^{\frac{1}{2}}$), 7.2 g of silicone resin which met the requirements specified in JAPANESE STANDARDS OF FOOD ADDITIVE 4th-Edition [said silicone resin being prepared by dispersing silicon dioxide at a concentration of 3–15 w/w % in dimethyl polysiloxane (viscosity measured at 25°:100–1,100 cSt)], 20 g of ethylcellulose (the ethoxy content and viscosity are the same as defined in Example 1) and 240 g of vitamin C having a particle size of 105–250 μm were added to 800 ml of cyclohexane. The mixture was stirred at 80° C. to give a dispersion of the core material (i.e., vitamin C). The dispersion was cooled to room temperature (about 25° C.) under stirring at 300 rpm. The microcapsules thus formed were recovered by filtration, washed with n-hexane and dried. Then, said microcapsules were passed through the nest of JIS standard sieve (350 μm aperture), whereby 254 g of vitamin C-containing microcapsules which met the requirements of "Pulvers" specified above were obtained.

EXAMPLE 6

24 g of polybutene (molecular weight: 1,000; δ=8.4 $(cal/cm^3)^{\frac{1}{2}}$), 20 g of ethylcellulose (the ethoxy content and viscosity are the same as defined in Example 1) and 200 g of diltiazem hydrochloride (chemical name: d-3-acetoxy-cis-2,3-dihydro-5-[2-(dimethylamino)ethyl]-2-(p-methoxyphenyl)-1,5-benzothiazepin-4(5H)-one hydrochloride) having a particle size of 105–210 μm were added to 800 ml of cyclohexane. The mixture was stirred at 80° C. to give a dispersion of the core material (i.e., diltiazem hydrochloride). The dispersion was cooled to a room temperature (about 25° C.) under stirring at 300 rpm. The microcapsules thus formed were recovered by filtration, washed with n-hexane and dried. Then, said microcapsules were passed through the nest of JIS standard sieve (350 μm aperture), whereby 216 g of diltiazem hydrochloride-containing microcapsules which met the requirements of "Pulvers" specified above were obtained.

EXAMPLE 7

16.8 g of liquid paraffin (δ=8.3–9.1 $(cal/cm^3)^{\frac{1}{2}}$), 7.2 g of silicone resin (said silicone resin being the same as that of Example 5), 20 g of ethylcellulose (the ethoxy content and viscosity are the same as defined in Example 1) and 140 g of 1-methyl-5-methoxy-3-(dithien-2-ylmethylene)piperidine hydrobromide (core material) having a particle size of 105–350 μm were added to 800 ml of cyclohexane. The mixture was stirred at 80° C. to give a dispersion of the core material. The dispersion was cooled to room temperature (about 25° C.) under stirring at 300 rpm. The microcapsules thus formed were recovered by filtration, washed with n-hexane and dried. Said microcapsules were passed through the nest of JIS standard sieve (500 μm aperture) and then the nest of JIS standard sieve (105 μm aperture). The microcapsules which passed through the former sieve but did not pass through the latter sieve were collected, whereby 152 g of 1-methyl-5-methoxy-3-(dithien-2-ylmethylene)piperidine hydrobromide-containing microcapsules which met the requirements of "Fine Granules" specified in THE PHARMACOPOEIA of JAPAN 10th-Edition were obtained.

For comparision, microcapsules were prepared in the same manner as described above except that 24 g of silicone resin were used instead of 16.8 g of liquid paraffin and 7.2 g of silicone resin, whereby only 27 g of 1-methyl-5-methoxy-3-(dithien-2-ylmethylene)piperidine hydrobromide-containing microcapsules which met the requirements of "Fine Granules" specified above were obtained.

What we claim is:

1. A method of preparing free-flowing microcapsules which comprises
   (i) dispersing particles of a core material in a cyclohexane solution containing ethylcellulose and a hydrocarbon compound, said hydrocarbon compound being soluble in cyclohexane and present in an amount of 0.1 to 20 grams per 100 ml of cyclohexane, said hydrocarbon compound further having a molecular weight of 150 to 3,000 and a solubility parameter (δ, at 25° C.) of 7 to 10 $(cal/cm^3)^{\frac{1}{2}}$, to form a dispersion,
   (ii) cooling said dispersion until ethylcellulose separates out from said dispersion to form coating walls on said particles of said core material to form microcapsules.

2. The method according to claim 1, wherein said hydrocarbon compound has a solubility parameter of 7.5 to 9.5 $(cal/cm^3)^{\frac{1}{2}}$.

3. The method according to claim 1, wherein said hydrocarbon compound has a solubility parameter of 8.0 to 9.2 $(cal/cm^3)^{\frac{1}{2}}$.

4. The method according to claim 1, wherein said hydrocarbon compound is a member selected from the group consisting of liquid paraffin petroleumjelly, ceresin, paraffin, microcrystalline wax, squalane, squalene, pristane, polybutadiene (Molecular weight: 500 to 3,000), polybutene (Molecular weight: 200 to 3,000), polyisoprene (Molecular weight: 1,000 to 3,000) and butadiene-styrene copolymer (Molecular weight: 1,500 to 3,000).

5. The method according to claim 1, wherein said hydrocarbon compound is a member selected from the group consisting of liquid paraffin, paraffin and polybutene (Molecular weight: 200 to 2,500).

6. The method according to claim 1, wherein said hydrocarbon compound is liquid paraffin.

7. The method according to claim 1, wherein the hydrocarbon compound is used in an amount of 1 to 10 g per 100 ml of cyclohexane.

8. The method according to claim 1, wherein the hydrocarbon compound is used in an amount of 1 to 3 g per 100 ml of cyclohexane.

9. The method according to claim 1, wherein ethylcellulose having an ethoxy content of 46.5 to 55 w/w % is used.

10. The method according to claim 1, wherein ethylcellulose having an ethoxy content of 46.5 to 55 w/w % and a viscosity (measured at 25° C. with respect to a 5 w/w % solution of it in toluene-ethanol (4:1)) of 3 to 500 cP is used.

11. The method according to claim 9, wherein ethylcellulose is used in an amount of 0.03 to 5 grams per gram of the core material.

12. The method according to claim 11, wherein the hydrocarbon compound is liquid paraffin.

13. The method according to claim 4, wherein the dispersing step (i) is carried out by adding ethylcellulose, the hydrocarbon compound and the core material to cyclohexane and then heating the mixture to 75° to 80° C.

14. The method according to claim 4, wherein the dispersing step (i) is carried out by dissolving ethylcellulose and the hydrocarbon compound in cyclohexane at 75° to 80° C. and then dispersing the core material in the solution under stirring.

15. The method according to claim 4, wherein the hydrocarbon compound is used in combination with a hydrocarbon polymer selected from the group consisting of butyl rubber, polybutadiene, polyethylene and polyisobutylene, said hydrocarbon polymer having a molecular weight of 4,000 to 2,000,000.

16. The method according to claim 4, wherein the hydrocarbon compound is used in combination with an organopolysiloxane selected from the group consisting of dimethyl polysiloxane, methylphenyl polysiloxane, diphenyl polysiloxane and polystyrene-polydimethylsiloxane block copolymer.

17. The method according to claim 15, wherein the hydrocarbon polymer is used in an amount of 0.1 to 10 grams per 100 ml of cyclohexane.

18. The method according to claim 16, wherein the organopolysiloxane is used in an amount of 0.01 to 10 grams per 100 ml of cyclohexane.

19. A method of preparing free-flowing microcapsules which comprises
  (i) dispersing particles of a core material in a cyclohexane solution containing ethylcellulose and a hydrocarbon compound, said hydrocarbon compound being soluble in cyclohexane and present in an amount of 0.1 to 20 grams per 100 ml of cyclohexane, said hydrocarbon compound further having a molecular weight of 150 to 3,000 and a solubility parameter ($\delta$, at 25° C.) of 7 to 10 $(cal/cm^3)^{\frac{1}{2}}$, to form a dispersion.
  (ii) cooling said dispersion until ethylcellulose separates out from said dispersion to form coating walls on said particles of said core material to form microcapsules, and then
  (iii) recovering said microcapsules from said dispersion.

* * * * *